United States Patent
Fox

(10) Patent No.: US 7,637,872 B1
(45) Date of Patent: Dec. 29, 2009

(54) BONE MARROW ASPIRATION AND BIOMATERIAL MIXING SYSTEM

(76) Inventor: William Casey Fox, 17412 Hwy. 16 South, Pipe Creek, TX (US) 78063

( * ) Notice: Subject to any disclaimer, the term of this patent is extended or adjusted under 35 U.S.C. 154(b) by 1186 days.

(21) Appl. No.: 10/408,633

(22) Filed: Apr. 7, 2003

(51) Int. Cl.
*A61B 10/00* (2006.01)
(52) U.S. Cl. ......................................... 600/562; 600/36
(58) Field of Classification Search ......... 600/562–568, 600/36
See application file for complete search history.

(56) References Cited

U.S. PATENT DOCUMENTS

| | | | |
|---|---|---|---|
| 3,844,272 A * | 10/1974 | Banko | 600/566 |
| 4,513,754 A | 4/1985 | Lee | |
| 4,630,616 A | 12/1986 | Tretinyak | |
| 5,106,364 A * | 4/1992 | Hayafuji et al. | 604/22 |
| 5,385,151 A | 1/1995 | Scarfone et al. | |
| 5,505,210 A * | 4/1996 | Clement | 600/566 |
| 5,526,822 A * | 6/1996 | Burbank et al. | 600/567 |
| 6,478,751 B1 * | 11/2002 | Krueger et al. | 600/566 |
| 6,796,957 B2 * | 9/2004 | Carpenter et al. | 604/93.01 |
| 2003/0176811 A1 * | 9/2003 | Shapira | 600/565 |
| 2004/0153005 A1 * | 8/2004 | Krueger | 600/571 |

OTHER PUBLICATIONS

Myers Bone Biopsy Needle. Cook Product literature, 1999.
Ackermann Biopsy Needle. Cook Product literature, 2001.
Osteo-Site(tm) Bone Biopsy Needle Set with side bevel. Cook Product literature, 2000.
Osteo-Site(tm) Bone Biopsy Needle Set with biamond bevel. Cook Product literature, 2000.
Rochester Bone Biopsy(tm) Trephine and Bone Graft Device. Medical Innovations.com product literature, Aug. 4, 2003.
Imbibe BoneMarrow Aspiration Syringe. Orthovita Product Literature 2 pages, Mar. 18, 2003.

* cited by examiner

*Primary Examiner*—Max Hindenburg
*Assistant Examiner*—Jonathan M Foreman
(74) *Attorney, Agent, or Firm*—King & Spalding

(57) ABSTRACT

Devices and methods for bone marrow aspiration, storage, and the combining of harvested marrow with biomaterials, therapeutic agents or medical devices are provided for the treatment or assessment on a variety of diseases or injuries. In a preferred embodiment, the invention includes aspiration of marrow into a cartridge to minimize bacterial contamination and clotting while facilitating handling, storage or the combining of harvested material with biomaterials, therapeutic agents or medical devices.

10 Claims, 9 Drawing Sheets

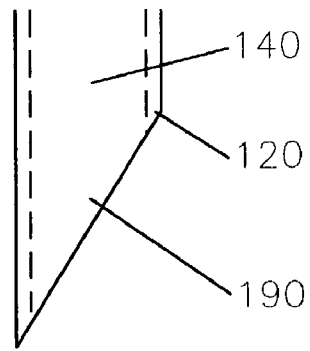 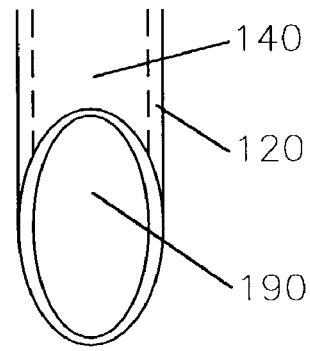
Fig 5a.    Fig 5b.
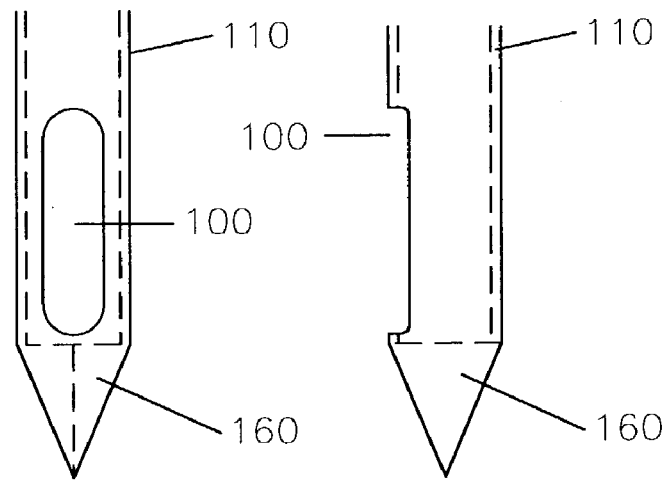
Fig 5c.    Fig 5d.

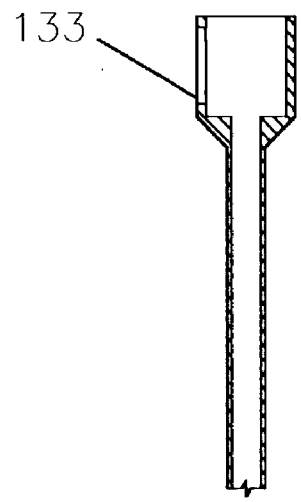
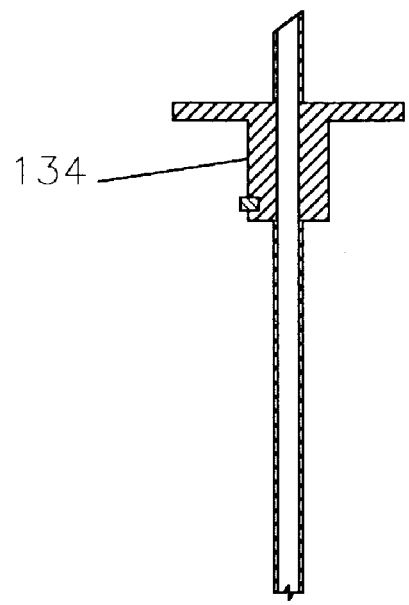
Fig. 8a.  Fig. 8b.
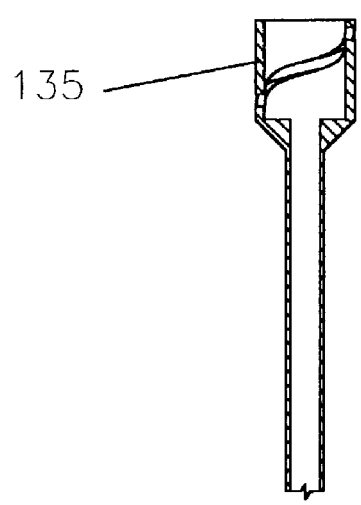
Fig. 8c.

ured States Patent US 7,637,872 B1

BONE MARROW ASPIRATION AND BIOMATERIAL MIXING SYSTEM

FIELD OF THE INVENTION

The present invention relates generally to fields of medicine having to do with obtaining, storing, and treating bone marrow, i.e., the fields of oncology, orthopaedic surgery, or radiology. More particularly, the invention concerns devices and methods for bone marrow aspiration, storage, and the combining of harvested marrow with biomaterials or medical devices. In a preferred embodiment, the invention includes aspiration of marrow into a cartridge to minimize bacterial contamination and clotting while facilitating storage or the combining of harvested material with biomaterials or medical devices.

BACKGROUND OF THE INVENTION

Specimens of bone, marrow, and fluids present in the medullary cavity of bone are biopsied to diagnose various diseases and harvested for medical treatment. These specimens are difficult to obtain since human bone has a hard outer cortex. Traditionally, marrow has been removed with large bore needles. A needle with an inserted stylet is pushed through an incision in the patient's skin and pressed through the muscle tissue and cortex of bone. The stylet is withdrawn and a syringe is attached to the needle. Bone marrow fluid is drawn using negative pressure. The needle may be gyrated to free the marrow sample for withdrawal.

Aspiration and biopsies are most commonly performed on the hip bone in adults and in long bones such as the femur in adolescents. Devices and systems for bone marrow tissue collection and processing for transplantation have been described. U.S. Pat. No. 5,199,942 to Gillis relates to a method for autologous hematopoietic cell transplantation of patients receiving cytoreductive therapy. U.S. Pat. Nos. 4,486,188, and 4,481,946 to Altshuler relate to an apparatus and method using a pair of needles, one to aspirate and a second to infuse intravenous solutions into bone. The apparatus reportedly has chambers, a fluid flow controller, valves, and syringes. The method appears to use simultaneous aspiration and infusion to recover bone marrow. Altshuler (U.S. Pat. No. 4,366,822) relates to the removal and separation of bone marrow cells by interposing a filtration chamber between a bone marrow needle and aspirator.

Baldridge (U.S. Pat. No. 5,357,974) relates to a bone marrow biopsy instrument including a hollow aspirate needle, a hollow biopsy needle telescoped within the aspirate needle and a solid stylet removably telescoped within the biopsy needle. U.S. Pat. No. 5,282,477 to Bauer relates to a device for performing a bone marrow biopsy such that it is possible to know during the biopsy whether tissue has been removed from the patient. Lee (U.S. Pat. No. 4,513,754) relates to a biopsy device that reportedly allows for the interchange of single-use needles.

Bone marrow biopsy needles and biopsy needles are common in the prior art. U.S. Pat. Nos. 3,477,423; 4,142,517; 4,356,828; 4,630,616; 5,012,818; 5,385,151; 5,394,887; and 5,538,009; and PCT publication WO 91/06246 relate to the general structure and orientation of components of biopsy needles.

Problems with prior art bone marrow harvest and manipulation devices include mechanical designs that allow exposure of marrow to air or unsterile surroundings during harvest, storage, and mixing of harvested bone marrow with any other biomaterial; inadequate storage or inefficient devices for mixing freshly harvested, tissue with biomaterials. Because of such problems, known procedures are not completely satisfactory, and the present inventor has searched for improvements.

SUMMARY OF THE INVENTION

The present invention seeks to overcome these and other drawbacks inherent in the prior art by providing a catheter/needle combination tip and bone marrow collection device that allow a completely enclosed sterile system for harvesting bone marrow, for storage of harvested marrow, and for mixing harvested marrow with a further biomaterial.

Accordingly, the present invention provides a bone marrow aspiration device comprising a catheter having a bore and a port; a needle having a bore and a port, the needle being fittable into the catheter bore and, when fitted, is rotatable or translatable relative to the catheter so as to move the catheter port and the needle port between an open port position and a closed port position; a housing having a bore, the housing capable of being rotationally or translationally coupled to the needle; and a suction conduit attachable to the housing. When in use, bone marrow is moved by aspiration from within bone through the open port position into the needle bore and into the housing bore.

The bone marrow aspiration device may further comprise a cartridge fittable into the housing, the cartridge having a cartridge bore, wherein, when in use, bone marrow is moved by aspiration from within bone through the open port position into the needle bore and into the cartridge bore. The cartridge may be prepackaged with a biomaterial, may be disposable, and is preferably provided as a sterile, single-use unit. Either embodiment of the bone marrow aspiration device, i.e., with or without the cartridge, may further comprise a cap rotatably or translatably attachable to the housing; may further comprise a mixing apparatus to form a bone marrow aspiration device and biomaterial mixing system; the cap may be a tissue processing apparatus; the cap may comprise a compartment for biomaterial storage; and the device may be sterile. Where the embodiment has both a cap and a cartridge, the cap and cartridge may be rotatable with respect to the housing to enhance mixing within the cartridge.

In further embodiments of the bone marrow aspiration device, the device may further comprise a structure that eliminates blocking of the suction conduit during use, the housing or the cartridge may comprise a compartment for biomaterial storage, or the housing or the cartridge may further comprise a biomaterial for mixing with harvested bone marrow.

The catheter port may be an end-port having a cut selected from the group consisting of an angle cut and a straight cut, and, in this case, the needle port is a side-port. The needle port may be an end-port, and, in this case, the catheter port is a side-port. Where the needle port is an end-port and a side-port, the catheter port is a side-port.

In a particularly preferred embodiment, a bone marrow aspiration device is provided; the device comprises a catheter having a first end and a second end, a catheter bore, and a catheter coupler at the second end; a needle having a first end and a second end, a needle bore, and a needle coupler at the second end for coupling to the catheter coupler and to a housing; wherein the catheter and the needle each have at the first end either an end-port, or a closed trocar cutting tip and a side-port adjacent the cutting tip; a housing having a housing bore, the housing capable of being coupled to the needle coupler; and a cap rotatably attachable to the housing, the cap having a suction conduit. When the catheter has an end-port, the needle has a closed trocar cutting tip and a side-port; and when the catheter has a closed trocar cutting tip and side-port, the needle has an end-port, such that when the needle is fitted into the catheter bore, the needle and the catheter and are rotatable or translatable relative to each other between a closed position where an end-port is not open to a side-port, and an open position where an end-port is open to a side-port and, when in use, bone marrow is moved by aspiration from within bone through an open port position, through a side-port, through the needle bore and into the housing bore. This preferred embodiment may further comprise a cartridge fittable into the housing bore, and, when in use, bone marrow is moved by aspiration from within bone through an open port position, through a side-port, through the needle bore and into the cartridge bore.

A bone marrow aspiration device and biomaterial mixing system is an aspect of the invention. The device and mixing system comprises the bone marrow aspiration device as described herein and a mixing apparatus positioned within the housing or the cartridge. When in use, bone marrow is moved by aspiration from within bone through the open port position into the needle bore and into the housing bore or cartridge bore and is available for mixing. The bone marrow aspiration device and biomaterial mixing system may further comprise a biomaterial within the housing or cartridge for mixing with harvested bone marrow.

A catheter/needle combination tip for bone marrow aspiration is a further aspect of the present invention. The combination tip comprises a catheter having a first end and a catheter bore; and a needle having a first end and a needle bore, the needle being fittable into the catheter bore. The catheter and the needle each have at the first end either an end-port or a closed trocar cutting tip and a side-port adjacent the cutting tip. When the catheter has an end-port, the needle has a closed trocar cutting tip and a side-port; and when the catheter has a closed trocar cutting tip and side-port, the needle has an end-port; such that when the needle is fitted into the catheter bore, the needle and the catheter and are rotatable or translatable relative to each other between a closed position where an end-port is not open to a side-port, and an open position where an end port is open to a side-port. For this embodiment of the catheter/needle combination tip, when the needle has an end-port, the needle further has a side-port adjacent the end-port.

In a further embodiment of the catheter/needle combination tip, the needle and the catheter each further have a second end, and the needle second end further comprises a coupler for rotationally or translationally coupling to the catheter second end, and for rotationally or translationally coupling to an aspiration source; and the catheter second end further comprises a coupler for rotationally or translationally coupling to the needle second end. An aspiration source may be a syringe, or a connection to suction such as a vacuum line, for example.

A bone marrow aspiration device comprising the catheter/needle combination tip herein described is another embodiment of the present invention. The device further comprises a housing having a housing bore, the housing capable of being coupled to the needle coupler and capable of being attached to a suction conduit; and a suction conduit. When in use, bone marrow is moved by aspiration from within bone through the needle bore and into the housing bore.

A method of obtaining bone marrow from a subject using a bone marrow aspiration device of the present invention is a further aspect of the invention. The method comprises the steps of attaching a suction source to the suction conduit of an assembled bone marrow aspiration device of the present invention; inserting the device into bone so that an opened position of the needle and catheter is within bone marrow; rotating or translating the catheter or the needle to form an open port position; and collecting bone marrow into the housing by applying suction to the device. The method may further comprise the step of inserting a cartridge into the housing; or where the cap or housing contains a biomaterial, the method may further comprise the step of rotating the cap with respect to the housing to mix the biomaterial with collected bone marrow.

In use, the bone marrow aspiration device includes a needle within a catheter, the needle and catheter interacting so as to open and close the needle lumen. This device further includes a fillable housing or a fillable tissue collection cartridge that fits into the housing, a cap and a suction port. The needle and catheter combination tip serves multiple functions: first, it acts as a trocar to cut through soft-tissue or bone; second, it provides a conduit between bone and the outside of the body; and third, it is a valve to open or close the needle lumen. The suction conduit communicates with the inside of the housing or cartridge to allow applied suction to draw bone marrow up the needle lumen and into the housing or cartridge for storage. This apparatus facilitates soft tissue and bone puncture, aspiration of bone marrow, storage of harvested marrow, and the combining of harvested marrow with a biomaterial or medical device.

The cartridge, housing, or cap can further be configured with a mixing apparatus, for example, a paddle, blade, flute, bead, finger, plunger, or the like, to facilitate mixing of an agent with harvested bone marrow. Additionally, the cartridge, housing, or cap can be configured with a compartment having a penetrable barrier such as a valve, seal, cap, or diaphragm, for example. The compartment may contain, separated from the marrow, an active agent or biomaterial. In use, the penetrable barrier separates the marrow from the agent until the mixing apparatus is engaged to breach the barrier and mix the marrow with the agent or biomaterial.

Collected bone marrow can be combined with antibiotics, anticoagulants, growth factors, anti-inflammatories, agents that may enhance tissue storage or viability, biomaterials of diverse shape and structure, or the like. Solid, porous, fibrous, gelatinous, or fluid materials can be stored in the cartridge and mixed with bone marrow during the aspiration procedure. U.S. Pat. No. 5,199,942 is incorporated by reference herein for teachings regarding use of growth factors relating to bone marrow.

Further, components of the aspiration device such as the tip, housing, or cap, for example, can be rotated or translated to facilitate mixing. The housing, which may be elongated in a preferred embodiment, has the catheter/needle combination tip on a first end and may have a cap with suction port on a second end. The cap may be removable and can engage the cartridge or mixing apparatus so as to stir the marrow into an agent or biomaterial.

The suction port may be designed to remain clear by providing a baffle, a filter, or other internal structure that prohibits harvested material from moving into the suction port. Such a structure would eliminate blocking of the suction tube, and loss of semisolid bone tissue and free fluid. The baffle, filter, or other structure can be combined to selectively filter the marrow aspirate so as to enhance its handling properties and mode of action when used as a transplant tissue.

The aspiration system allows indirect manipulation of the tissue and mixing apparatus by the surgeon. Indirect manipulation may include actions such as turning or translating the combination tip, housing, or cap, or shaking the aspiration device once removed from the patient. Suction and flow of air and tissue through the device may further facilitate mixing.

The device of the invention can be disposable or be designed for multi-patient use. The cartridge can be prepackaged with agents or biomaterials, or filled operatively. The device is fabricated out of a biocompatible material such as a plastic, an elastomer, a metal, or a ceramic, for example. "Plastic", as used herein, includes but is not limited to polycarbonate, acrylic, methylmethacrylate, polyurethane, nylon, delrin, or TEFLON☐, for example. "Elastomer", as used herein, includes but is not limited to silicone, or rubber, for example. "Metal", as used herein, includes but is not limited to stainless steel, titanium, chromium cobalt, or derivatives thereof. "Ceramic", as used herein, includes but is not limited to silica glasses, calcium carbonate, or calcium phosphate, for example.

In a preferred embodiment, the method of the present invention includes sharp trocar dissection of the soft-tissue, sharp interosseous entry, bone marrow needle aspiration, marrow collection, and tissue mixing within a clean, sterile and optimized environment. This system allows for collection and optimization of bone marrow without direct manipulation by the surgeon. Direct manipulation means manipulating with human hands, a spatula, in a bowl or other means that generally exposes the tissue to air or surgical instruments.

Following long-standing patent law convention, the terms "a" and "an" mean "one or more" when used in this application, including the claims.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 5a-FIG. 5d show a component exploded view of the tip of the aspiration device of FIG. 1 having an embodiment incorporating a catheter/needle combination tip for bone marrow collection. FIG. 5a-FIG. 5b show the tip of catheter 120 having an angled cut 190 for use with needle 110 of FIG. 5c and FIG. 5d. Needle 110 has needle trocar cutting tip 160 and needle side-port 100. When assembled, rotational or translational movement of catheter 120 relative to needle 110 aligns catheter tip 190 and needle side-port 100 for aspiration.

FIG. 6a and FIG. 6b show catheter 121 having catheter trocar tip 111, catheter side-port 101 for use with needle 112 of FIG. 6c and FIG. 6d. Needle 112 has end port 102 and side-port 100. When assembled, rotational movement of catheter 121 relative to needle 112 aligns catheter side-port 101 and needle side-port 100 for aspiration; further, translational movement of catheter 121 relative to needle 112 allows access to needle end-port 102 allowing aspiration.

FIG. 8a shows a further embodiment of a catheter 133 allowing translation and FIGS. 8b and 8c show catheter 135 that allows both rotational and translational movement when used with needle 134.

Figure 1:
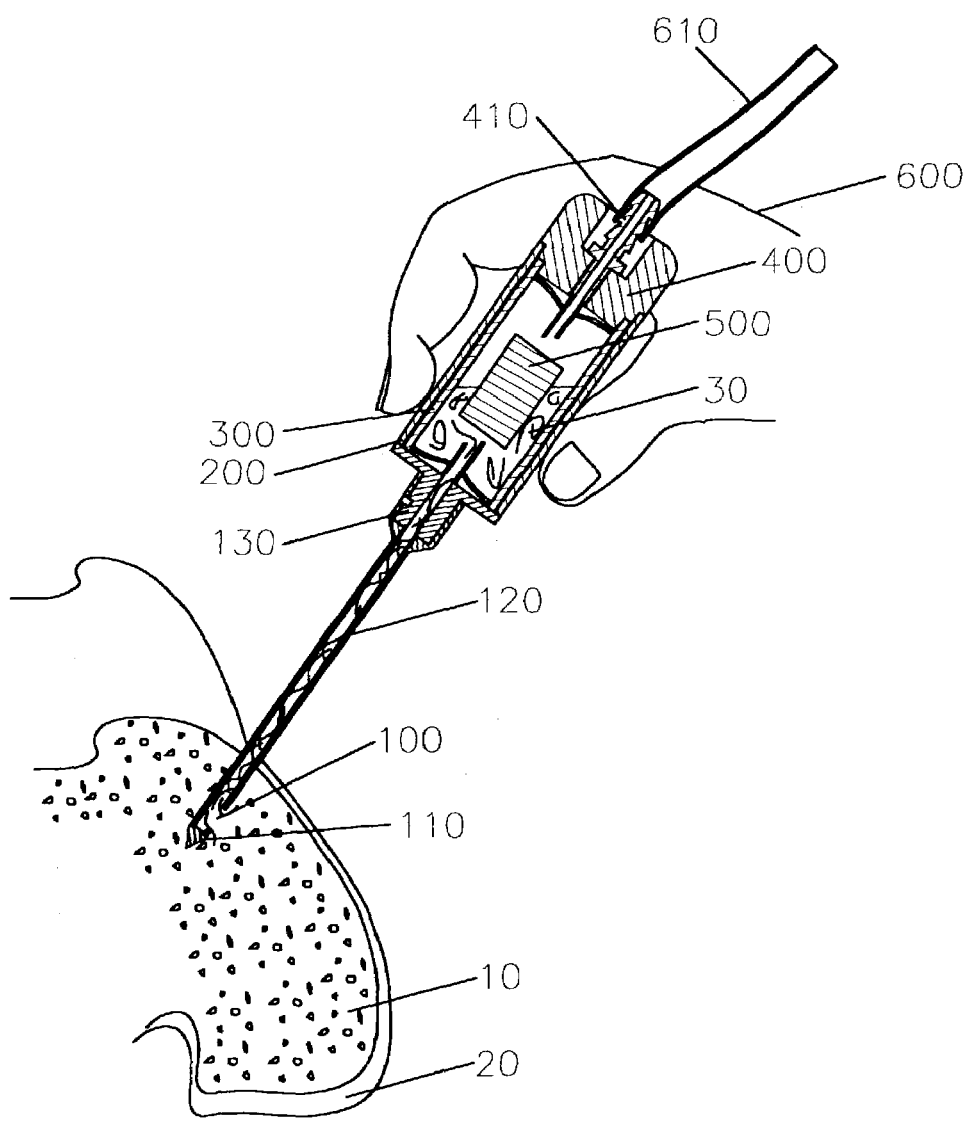
FIG. 1 provides an illustrated cross-sectional view of an aspiration device of the present invention in use. A human hand 600 is shown holding the device in bone 10 and 20 while bone marrow 30 is suctioned into a cartridge 300 and mixed with a solid biomaterial 500.
Figure 2:
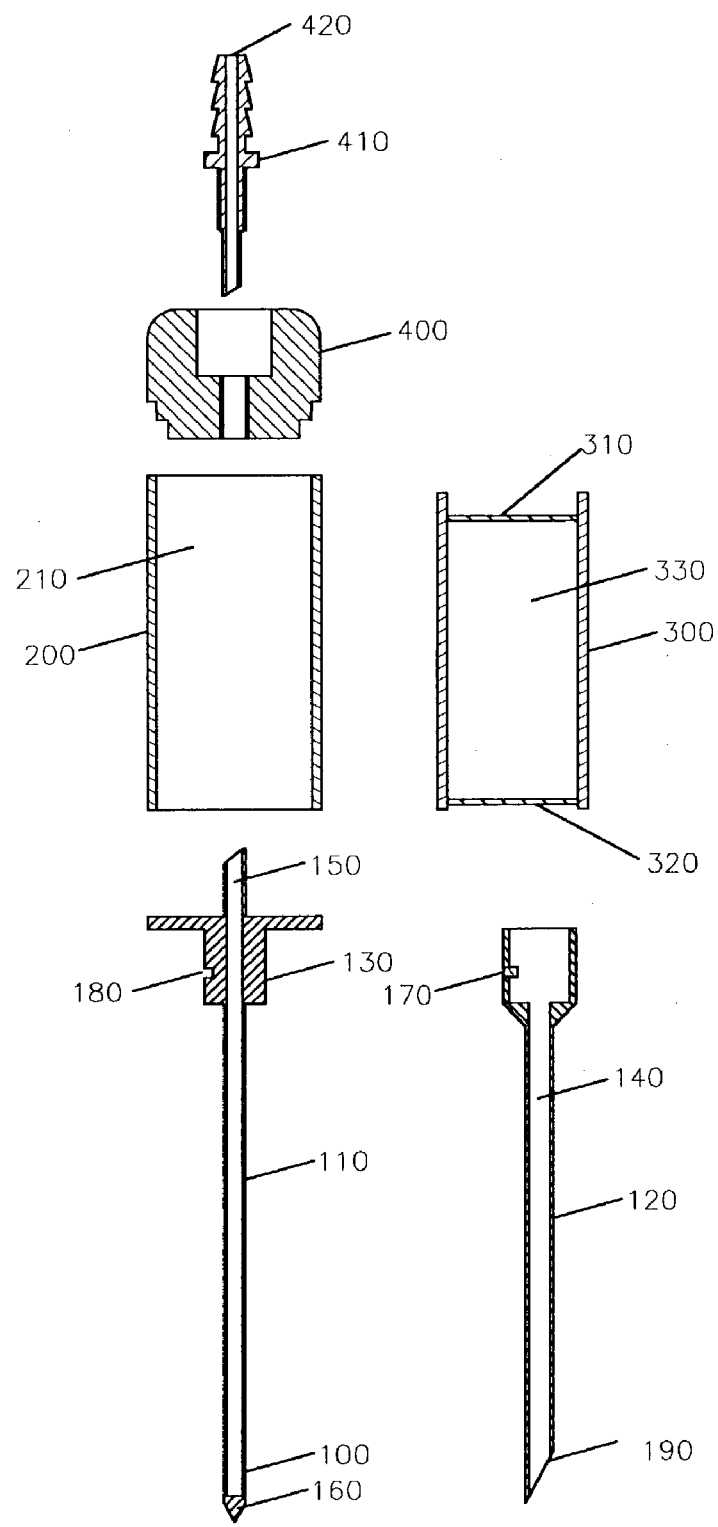
FIG. 2 provides an assembly view of the components of the aspiration device of FIG. 1 in a cross-sectional plane view showing suction conduit 410, cap 400, housing 200, cartridge 300, needle 110, housing coupler 130, and catheter 120 with rotational control mechanism including a rotational stop pin 170 and rotational groove 180.
Figure 3:
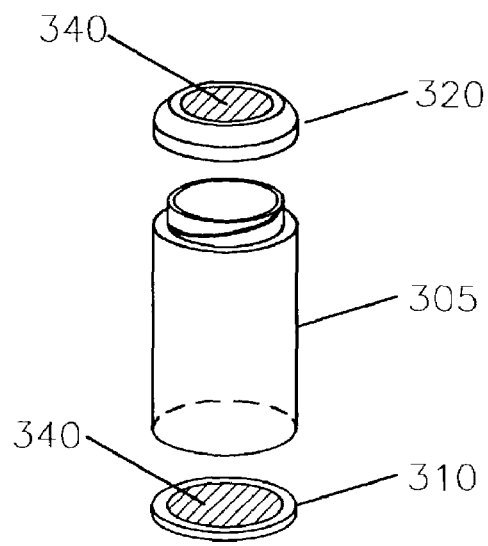
FIG. 3 shows an oblique view of a cartridge with cartridge housing 305, penetrable, removable, self-sealing end cap 320 and penetrable, movable end cap 310. Penetrable barrier 340 is shown integral to the end caps.
Figure 4:
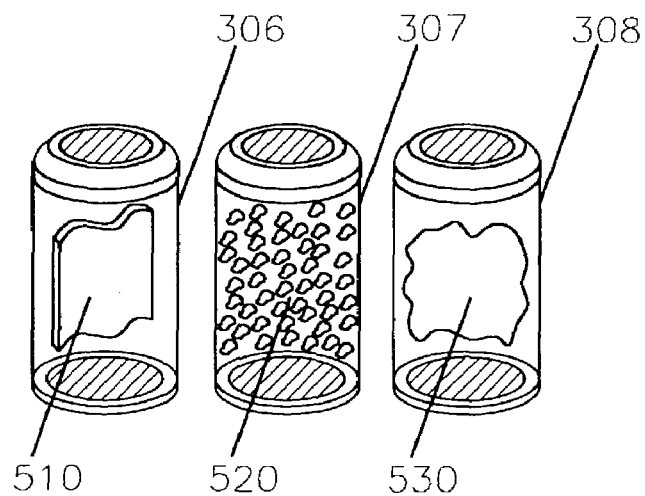
FIG. 4 provides an oblique view of cartridge 306 containing biomaterials in fiber sheet form 510, cartridge 307 containing biomaterials in particulate form 520, and cartridge 308 containing biomaterials in a putty consistency form 530.

LIST OF REFERENCE NUMERALS 10 cancellous bone and bone marrow tissue
20 cortical bone
30 bone marrow aspirate (tissue)
100 needle side-port
101 catheter side-port
102 needle end-port
110 needle with trocar cutting tip
111 catheter trocar tip
112 needle with end-port and side-port
113 needle with end-port
120 catheter with angle cut tip
121 catheter with trocar tip
130 catheter, needle and housing rotational coupler
133 catheter, needle and housing translational coupler
135 catheter, needle and housing rotational and translational coupler
140 catheter bore
150 needle bore
160 needle trocar cutting tip
170 rotational stop pin
180 rotational groove
190 catheter tip angle cut
200 housing
210 housing bore
300 cartridge
305 cartridge housing
306 cartridge with fiber sheet
307 cartridge with particulate
308 cartridge with putty
309 cartridge with mixing apparatus
310 penetrable and movable end cap
320 penetrable, removable and self-sealing end cap
330 cartridge bore
340 penetrable barrier
350 biomaterial compartment 360 internal penetrable barrier
370 tissue processing accessory
380 mixing apparatus
400 cap
410 suction conduit
420 suction port bore
500 solid biomaterial
510 fiber sheet biomaterial
520 particulate biomaterial
530 putty consistency biomaterial
540 biomaterial
600 human hand illustration
610 suction line
700 quick couple connector for syringe or suction line attachment
710 catheter with end-port and a plurality of side-ports
720 needle with a closed cutting tip and a plurality of side-ports
730 needle and catheter side ports in open position
740 needle side-port and catheter end-port in open position

DETAILED DESCRIPTION OF THE PREFERRED EMBODIMENTS

The present invention includes devices for penetrating soft-tissue and bone, for forming a conduit to bone marrow, for facilitating withdrawal of marrow, for containing harvested marrow, and for combining harvested marrow with further materials or devices.

An embodiment of an aspiration device of the present invention includes a tip, housing, and suction conduit. The device may further include a cartridge or cap. The tip may include needle 110, catheter 120, and housing coupler 130. In one embodiment, housing 200 may contain cartridge 300, may have a cap 400, and is ergonomically formed for human hand use. Housing 200 may be clear for viewing tissue. Suction conduit 410 is preferably formed to have a sharp tube for penetrating cartridge 300 at a first end and a connector for suction line 610 at a second end. Cap 400 may be removable from housing 200 and may contain suction conduit 410.

Figure 6A:
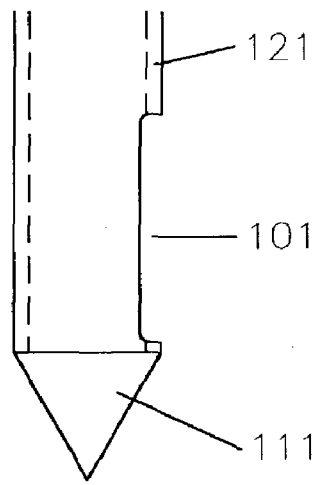
FIG. 6a-FIG. 6d show a further embodiment of a catheter/needle combination tip for a bone marrow aspiration device.
Figure 6B:
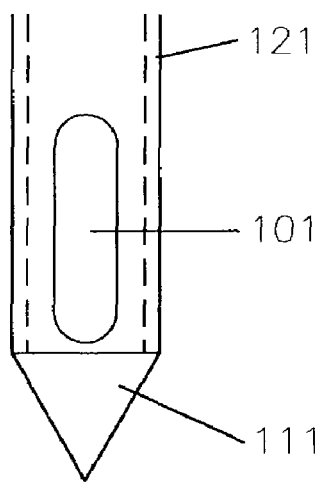
Figure 6C:
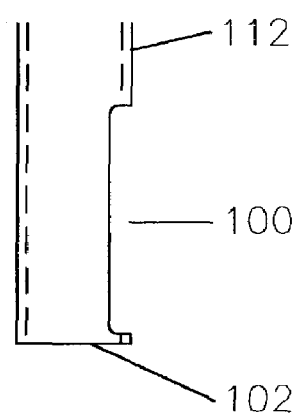
Figure 6D:
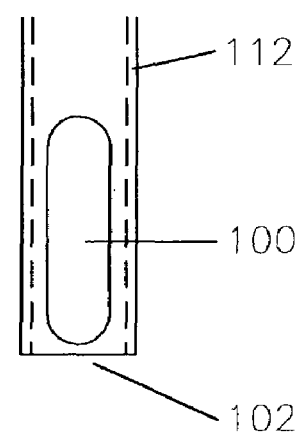
Figure 7:
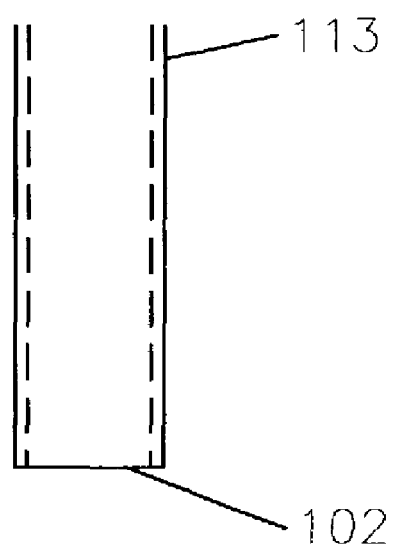
FIG. 7 provide a further embodiment of a needle for use with catheter 121 of FIG. 6a and FIG. 6b. Needle 113 has end-port 102; translational movement of needle 113 within catheter 121 opens catheter side-port 101 and allows aspiration. In this configuration, housing coupler 130 rotational control mechanism is replaced with a translational control mechanism or combined rotational and translational control mechanism.
Figure 9:
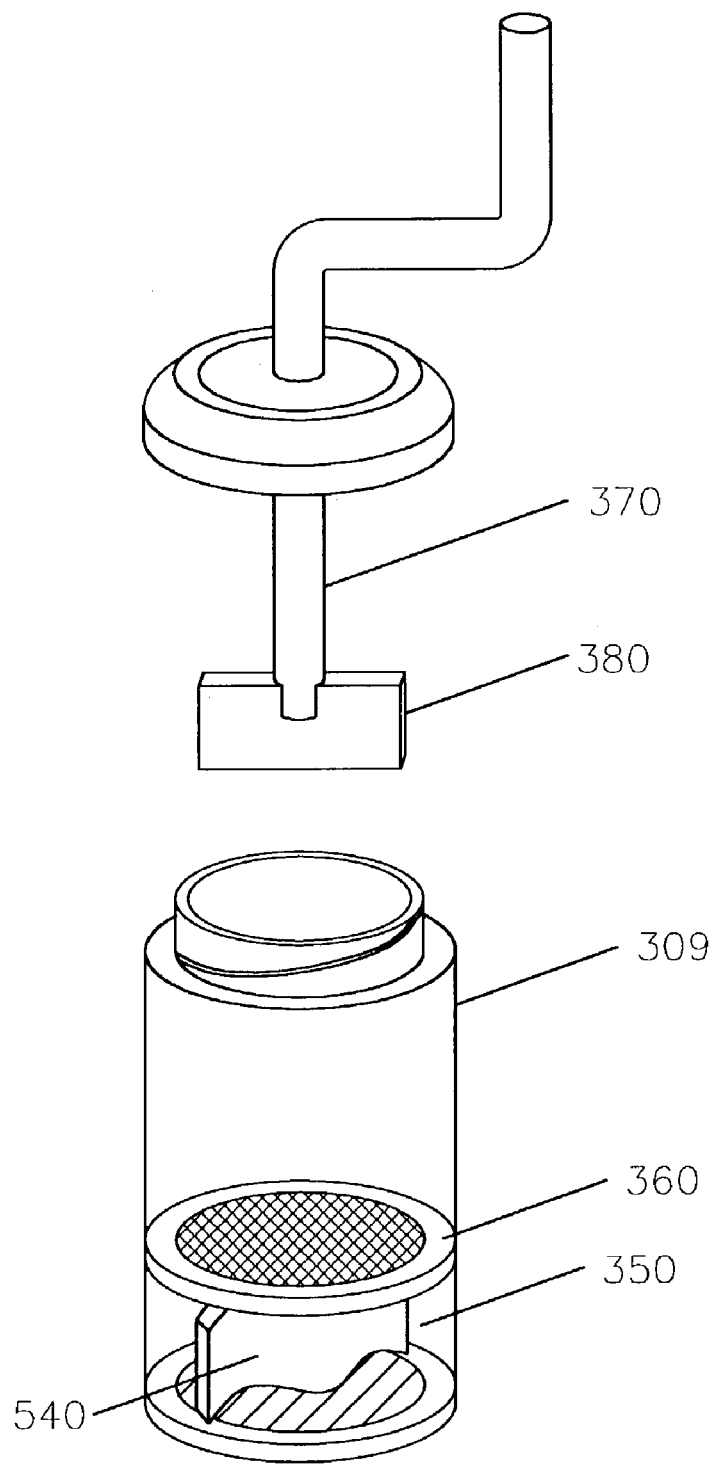
FIG. 9 shows cartridge 309 having biomaterial compartment 350, internal penetrable barrier 360, plunger 370, and mixing apparatus 380 for combining biomaterial 540 with bone marrow.
Figure 10:
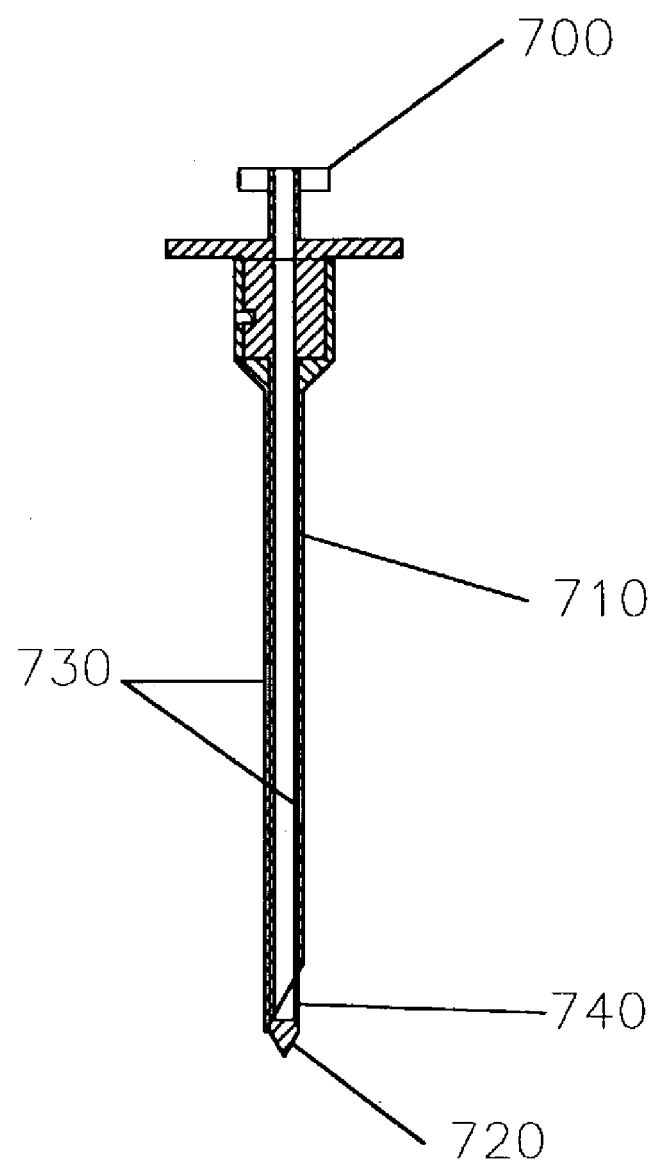
FIG. 10 shows an embodiment of an aspiration device of the present invention lacking a housing for the direct attachment of a syringe or suction line to the quick connect coupler 700 further showing the catheter 710, needle with closed sharp cutting tip 720, and the open position of the catheter end-port and needle side-port 740 and a plurality of open catheter and needle side ports 730.

In an embodiment of a catheter/needle combination tip, needle 110 and catheter 120 operate together to open and close needle side-port 100. Needle side-port 100 may also be described as a hole, or a slot into needle bore 150. Catheter 120 and needle 110 are of similar length and form two concentric tubes when assembled. When rotated or translated in relation to each other, ports become aligned allowing aspiration to occur. Catheter 120 may have an angled cut 190 at the tip, and needle 110 has a trocar cutting closed end tip 160 with side-port 100 near closed end 160. The outer surface of the closed end of the needle is formed with a trocar cutting tip 160. When assembled, needle 110 runs within catheter 120. When rotated, needle side-port 100 moves between an open position and a closed position as the side-port rotates from the open to closed side of catheter angled cut tip 190. When closed, needle 110 and catheter 120 form a sharp cutting tip. When needle 110 and catheter 120 are rotated or translated with respect to each other, an opening forms a notch which increases in area with rotation and translation until the maximum bore area is exposed. When rotated or translated, catheter 120 tends to clear tissue from the inner-running needle side-port 100. Together catheter 120 and needle 110 act with the housing coupler 130 to form a closeable conduit into housing 200 and a sharp surgical instrument at the tip of the aspiration device. A further embodiment of a catheter/needle combination tip is demonstrated in FIGS. 6a-6d where catheter 121 has catheter trocar tip 111 and catheter side-port 101; needle 112 has needle side-port 100 and needle end-port 102. Needle 113 having end-port 102 is also used with catheter 121; needle 113 may have end-port 102 cut at an angle or straight cut.

Housing coupler 130 joins catheter 120 and needle 110 to housing 200, provides for rotational movement of needle 110 relative to catheter 120, and forms a conduit from needle bore 150 into housing 200 or cartridge 300. When housing 200 is fitted with cartridge 300, housing coupler 130 sharply protrudes into housing 200 so as to penetrate cartridge 300 and form a direct path for fluid flow from needle 110 tip to the inside of cartridge 300. Housing coupler 130 may be integral to housing 200 or, when a separate component, may be coupled to housing 200 using quick couple fittings, threads, glue, or a press-fitted structure, for example. Needle bore 150 and housing coupler 130 may be constructed so as to form an arrowhead-like structure at the housing end of needle 110; the arrowhead-like structure may include a structure to assist in penetrating penetrable barrier 340.

Housing 200 is preferably elongated, has housing bore 210, is able to be coupled to a needle/catheter combination tip on a first end, and is open on a second end. The housing exterior may be formed for being handheld. Housing 200 may be clear for tissue 30 viewing, or may have graduations so as to measure the volume of collected tissue 30. Housing 200 is designed to be used with or without a cartridge 300. A cap 400 or tissue processing accessory 370 and mixing apparatus 380 can be secured to the open end of the housing or one end of cartridge 300. Housing 200 may be designed to receive cartridge 300 into bore 210. When used with cartridge 300; housing 200, cartridge 300, and cap 400 interact so as to rotate the biomaterial to facilitate mixing with the aspirated marrow.

Cap 400 is removable from housing 200, and provides a suction conduit 410 for applying suction to housing 200 or to cartridge 300. Suction conduit 410 penetrates cartridge 300 at a first end and connects to a suction line 610 with a second end. Cap 400 has tabs, slots, or similar structures to engage cartridge 300. Such structures allow cap 400 and cartridge 300 to be movably fastened so as to allow cartridge 300 rotation and translation within housing 200.

Cartridge 300 can be used with cap 400 containing a filter or baffle system in suction conduit 410 to remove any semi-solid tissue 30 from the suction port bore 420.

Cartridge 300 fits into housing 200 and is engaged by cap 400. Counter-rotation of cap 400 and housing 200 turns cartridge 300 within housing 200. This rotational feature enhances mixing and is the preferred configuration for driving the cartridge 300 for mixing a biomaterial with the aspirated marrow. A further embodiment is a mixing apparatus 380 that can be inserted or incorporated into cartridge 300. Cartridge 300 is preferably elongated so as to fit into housing bore 210, has removable, movable, and penetrable end caps 310 or 320. Said end caps are removable for filling and removal of harvested tissue. End cap 310 can be movable so as to facilitate mixing or pushing out of harvested tissue 30. End caps may have penetrable barriers 340 so as to allow the sharp needle bore 150 of the combination tip or the sharp suction conduit 410 to enter the cartridge 300. Cartridge 300 may be clear to observe and measure harvested tissue 30, and may have graduations. Preferably, cartridge 300 is sterile. End caps 310 and 320 may be penetrable and self-sealing.

After harvest of bone marrow aspirate, cartridge 300 may be used with a dispenser that receives cartridge 300 and acts on movable end cap 310 so as to push tissue 30 from cartridge bore 330.

Further embodiments include an aspiration device without cartridge 300; a further catheter/needle combination tip having a similar mode of operation where catheter 121 has catheter side-port 101 and catheter trocar tip 111, while needle 112 has needle side-port 100 and needle end-port 102; a tissue processing accessory 370 and mixing apparatus 380 for housing 200 or cartridge 300; or housing compartment, cartridge biomaterial compartment 350 or cap compartments with an internal penetrable barrier 360 for agent or solid biomaterial 500 storage until mixing.

Rotational catheter coupler 130, translational catheter coupler 133 or combined rotational and translational catheter coupler 135 facilitate movement of the needle within the catheter to open a side-port or end-port and couple the catheter needle assembly to the housing or other accessory such as syringe, suction line 610 or other source of vacuum to facilitate the harvest of bone marrow.

The catheter/needle combination tip and bone marrow aspiration device is used during surgery to obtain bone marrow. The tip of the device is pushed through soft-tissue and cortical bone of the ilium 20, for example; the device is operated so as to open bore 150 of needle 110 and used with suction to draw bone marrow up needle 110 and into housing 200 or cartridge 300.

In conventional practice, an empty cartridge is inserted into the housing to collect bone marrow for storage or in vitro processing. A cartridge containing a biomaterial or a biologically active agent is used for the combining of harvested marrow with such biomaterial or active agent. The biomaterial or active agent may be a conductive matrix from the list including but not limited to formulations of calcium sulfate, calcium carbonate, calcium phosphate, collagen, human cadaver tissue and their mixtures or therapeutic agent from the list including but not limited to bone morphogenic proteins, transforming growth factor, platelet derived growth factor, fibroblast growth factor, heparin, or living cell seeded system.

To operate the aspiration device, cap 400 is removed, a cartridge 300 is inserted into housing 200, cap 400 is then placed on housing 200 so as to engage cartridge 300 and penetrate cartridge barrier 340 with tip needle bore 150 and cap suction conduit 410. Once cap 400 is secure on housing 200, suction hose 610 is attached to suction conduit 410. Needle 110 and catheter 120 are then oriented so as to close needle side-port 100 and form a cutting end with needle trocar tip 160 and catheter angle cut tip 190. The aspiration device can then be introduced into a body.

The catheter/needle combination cutting tip of the aspiration device is pushed through skin and cortical bone until the tip and needle side-port 100 are within cancellous bone and bone marrow tissue 10. In a particular embodiment, catheter 120 is turned so as to open needle side port 100 to allow suctioning of fluid into needle 110 and into housing 200 or cartridge 300. During movement of fluid into cartridge 300, cap 400 can be rotated with respect to housing 200 so as to turn and mix a solid biomaterial 500 or active agent with harvested marrow tissue 30.

Once marrow tissue 30 has been collected in housing 200 or cartridge 300, needle 110 and catheter 120 are reoriented so as to close needle side-port 100. Once needle side-port 100 is closed, the aspiration device is repositioned within cancellous bone and marrow tissue 10 or withdrawn from the body. Suction line 610 is then removed, and cap 400 is removed.

Tissue 30 may be withdrawn from cartridge 300 by penetrating end cap barrier 340 with needle, for example, while the marrow is being contained and kept sterile in the cartridge. Penetrable barriers 340 can seal so as to protect the marrow from environmental contamination or spillage. Further, cartridge 300 may be emptied by removal of end cap 320 and expulsion of tissue 30 from cartridge 300 by dumping harvested tissue into a recipient site, by pushing end cap 310 with a plunger, by installing cartridge 300 into a dispenser that uses a plunger, or by spooning harvested material from cartridge bore 330.

The aspiration device may be single-use and discarded following collection of bone marrow tissue 30 to eliminate risk of interpatient disease transmission.

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and the scope of the invention be embraced by the defined claims.

EXAMPLE I

Marrow Aspiration from Rabbits with a Syringe, Needle and Stylus System and Unprotected Mixing and Handling The first study of the developing device was used to harvest bone marrow from the iliac crest of rabbits for the mixture of the marrow with a biomaterial to enhance its biological properties. The initial design used a syringe, needle, needle bone stylus and biomaterial compartment. This design successfully harvested marrow but had the following deficiencies: the needle did not close its end port and thus it became blocked with bone, the syringe did not allow continuous aspiration and required the user to remove the device from the subject, empty a small harvest volume from the syringe start the harvest again, and only an end-port was used and blocked easily. This study resulted in a low volume harvest, inconvenience for the surgeon, no protection of the biomaterial and marrow from the environment and required mixing in a bowl outside of the subject invention. It was shown that the combination of marrow with this biomaterial did not significantly enhance bone healing in the rabbit spine.

EXAMPLE II

Marrow Enhancement of a Synthetic Bone Matrix with and without Heparin

In a second study of marrow harvest in rabbits the device of example I was modified to overcome several of the deficiencies of the previous system. It again used a syringe with biomaterial chamber, needle bone stylus attached to the plunger so that they worked together and end-port on the needle. This still required the surgeon to remove the device from the patient for each few cc of marrow harvested and did not sufficiently mix the marrow with the biomaterial and needle end-port obstruction still occurred. It was shown that marrow and marrow with heparin did not significantly enhance the ability of the biomaterial to enhance new bone formation in the spine of rabbits.

EXAMPLE III

Marrow Harvesting for Stem Cell Expansion for Orthopaedic Implant Seeding

Though marrow and marrow combined with heparin did not significantly enhance bone healing in the spinal treatment evaluated developing technology has provided data that indicates that concentrated marrow may have the desired bone healing effect. In a study in baboons marrow was harvested from juvenile animals using a needle with stylus and a quick couple connector for the attachment of a syringe. This system again required repeated aspiration and removal from the harvest site, exposure of the harvested marrow to room air, and suffered from blockage.

Though the system still suffered from many of the same deficiencies the concentrated marrow was seeded onto a biomaterial, implanted to heal a defect in the fibula of a baboon and show good efficacy at enhancing the biologic response and healing of the bone defect where implant materials without concentrated marrow did not become will incorporated into bone.

EXAMPLE IV

Prototype Marrow Aspiration and Biomaterial Mixing System

The prototype device of the subject invention was developed with the needle within a catheter, multiple ports into the bore of the needle, a housing and cartridge to collect the marrow, features for mixing within the device and the use of a suction line instead of using a syringe for suction. This system was used in models with simulated marrow and was shown to minimize port blockage, did not require a needle bore stylus to clear the needle, allowed the surgeon to enter the bony site and aspirate marrow from multiple sites within bone without removing the needle/catheter tip from the patient, allowed mixing of the biomaterial and marrow without opening the device and eased the surgeons task by using hospital supply suction versus creating suction by pulling a plunger within the bore of a syringe.

References cited herein, to the extent that they provide exemplary procedural or other details supplementary to those set forth herein, are specifically incorporated herein by reference.

What is claimed is:

1. A bone marrow aspiration device comprising
a catheter comprising a bore and a port;
a needle comprising a bore and a port, the needle being fittable into the catheter bore and, when fitted, is rotatable or translatable relative to the catheter so as to move the catheter port and the needle port between an open port position and a closed port position;
a housing comprising a bore, the housing capable of being rotationally or translationally coupled to the needle;
a cartridge fittable into the housing, the cartridge having a cartridge bore, wherein, when in use, bone marrow is moved by aspiration from within bone through the open port position into the needle bore and into the cartridge bore;
a cap rotatably or translatably attachable to the housing, wherein the cap comprises a compartment for biomaterial storage; and
a suction conduit attachable to the housing wherein, when in use, bone marrow is moved, by applied aspiration from within bone through the open port position into the needle bore and into the housing bore.

2. A bone marrow aspiration device comprising
a catheter comprising a bore and a port;
a needle comprising a bore and a port, the needle being fittable into the catheter bore and, when fitted, is rotatable or translatable relative to the catheter so as to move the catheter port and the needle port between an open port position and a closed port position;
a housing comprising a bore, the housing capable of being rotationally or translationally coupled to the needle;
a cartridge fittable into the housing, the cartridge having a cartridge bore, wherein, when in use, bone marrow is moved by aspiration from within bone through the open port position into the needle bore and into the cartridge bore; wherein the cartridge further comprises a biomaterial for mixing with bone marrow; and
a suction conduit attachable to the housing wherein, when in use, bone marrow is moved, by applied aspiration from within bone through the open port position into the needle bore and into the housing bore.

3. A bone marrow aspiration device comprising
a catheter comprising a bore and a port;
a needle comprising a bore and a port, the needle being fittable into the catheter bore and, when fitted, is rotatable or translatable relative to the catheter so as to move the catheter port and the needle port between an open port position and a closed port position;
a housing comprising a bore, the housing capable of being rotationally or translationally coupled to the needle;
a cartridge fittable into the housing, the cartridge having a cartridge bore, wherein, when in use, bone marrow is moved by aspiration from within bone through the open port position into the needle bore and into the cartridge bore; wherein the cartridge is prepackaged with a biomaterial; and
a suction conduit attachable to the housing wherein, when in use, bone marrow is moved, by applied aspiration from within bone through the open port position into the needle bore and into the housing bore.

4. A bone marrow aspiration device comprising
a catheter having a first end and a second end, a catheter bore, and a catheter coupler at the second end;
a needle having a first end and a second end, a needle bore, and a needle coupler at the second end for coupling to the catheter coupler and to a housing; wherein the catheter and the needle each have at the first end either an endport; or a closed trocar cutting tip and a side-port adjacent the cutting tip;
a housing having a housing bore, the housing capable of being coupled to the needle coupler; and
a cap rotatably attachable to the housing, the cap having a suction conduit: wherein when the catheter has an endport, the needle has a closed trocar cutting tip and a side port; and when the catheter has a closed trocar cutting tip and side-port, the needle has an end port, such that when the needle is fitted into the catheter bore, the needle and the catheter and are rotatable or translatable relative to each other between a closed position where an end-port or side-port is not open to a side-port and an open position where an end port or side-port is open to a side-port, and wherein, when in use, bone marrow is moved by applied aspiration from within bone through an open port position, through a side-port, through the needle bore and into the housing bore.

5. The bone marrow aspiration device of claim 4 further comprising a cartridge fittable into the housing bore, and wherein, when in use, bone marrow is moved by applied aspiration from within bone through an open port position, through a side-port, through the needle bore and into the cartridge bore.

6. A bone marrow aspiration device and biomaterial mixing system comprising
a catheter having a bore and a plurality of ports;
a needle having a bore and a plurality of ports, the needle being fittable into the catheter bore and, when fitted, is rotatable or translatable relative to the catheter so as to move the catheter port and the needle port between an open port position and a closed port position;

a housing having a bore, the housing capable of being rotationally or translationally coupled to the needle;

a suction conduit attachable to the housing; and a mixing apparatus positioned within the housing; wherein, when in use, bone marrow is moved by applied aspiration from within bone through the open port position into the needle bore and into the housing bore and is available for mixing.

7. The bone marrow aspiration device and biomaterial mixing system of claim 6 further comprising a biomaterial or a biologically active agent within the housing for mixing with harvested bone marrow.

8. A method of obtaining bone marrow from a subject comprising:

attaching a suction source to the suction conduit of an assembled bone marrow aspiration device comprising a catheter comprising a bore and a port;

a needle comprising a bore and a port, the needle being fittable into the catheter bore and, when fitted, is rotatable or translatable relative to the catheter so as to move the catheter port and the needle port between an open port position and a closed port position;

a housing comprising a bore and capable of being rotationally or translationally coupled to the needle; and a suction conduit attachable to the housing wherein, when in use, bone marrow is moved, without cutting, by applied aspiration from within bone through the open port position into the needle bore and into the housing bore;

inserting a cartridge into the housing;

inserting the device into bone so that an opened position of the needle and catheter is within bone marrow;

rotating or translating the catheter or the needle to form an open port position; and collecting bone marrow into the housing by applying suction to the device.

9. A method of obtaining bone marrow from a subject comprising:

attaching a suction source to the suction conduit of an assembled bone marrow aspiration device comprising a catheter comprising a bore and a port;

a needle comprising a bore and a port, the needle being fittable into the catheter bore and, when fitted, is rotatable or translatable relative to the catheter so as to move the catheter port and the needle port between an open port position and a closed port position;

a housing comprising a bore and capable of being rotationally or translationally coupled to the needle;

a cap rotatably or translatably attachable to the housing;

a suction conduit attachable to the housing; and a cartridge fittable into the housing, the cartridge having a cartridge bore, wherein, when in use, bone marrow is moved. without cutting, by aspiration from within bone through the open port position into the needle bore and into the cartridge bore;

inserting the device into bone so that an opened position of the needle and catheter is within bone marrow;

rotating or translating the catheter or the needle to form an open port position;

collecting bone marrow into the housing by applying suction to the device; and rotating the cap with respect to the housing to mix a biomaterial with collected bone marrow, wherein the cap contains the biomaterial.

10. A method of obtaining bone marrow from a subject comprising:

attaching a suction source to the suction conduit of an assembled bone marrow aspiration device comprising a catheter comprising a bore and a port;

a needle comprising a bore and a port, the needle being fittable into the catheter bore and, when fitted, is rotatable or translatable relative to the catheter so as to move the catheter port and the needle port between an open port position and a closed port position;

a housing comprising a bore and capable of being rotationally or translationally coupled to the needle;

a cap rotatably or translatably attachable to the housing;

a suction conduit attachable to the housing; and a cartridge fittable into the housing, the cartridge having a cartridge bore, wherein, when in use, bone marrow is moved. without cutting, by aspiration from within bone through the open port position into the needle bore and into the cartridge bore;

inserting the device into bone so that an opened position of the needle and catheter is within bone marrow;

rotating or translating the catheter or the needle to form an open port position;

collecting bone marrow into the housing by applying suction to the device; and enhancing the biological properties of biomaterials and therapeutic agent with bone marrow.

\* \* \* \* \*

UNITED STATES PATENT AND TRADEMARK OFFICE
CERTIFICATE OF CORRECTION

| | | |
|---|---|---|
| PATENT NO. | : 7,637,872 B1 | Page 1 of 1 |
| APPLICATION NO. | : 10/408633 | |
| DATED | : December 29, 2009 | |
| INVENTOR(S) | : William Casey Fox | |

It is certified that error appears in the above-identified patent and that said Letters Patent is hereby corrected as shown below:

Claim 9, Column 14, Line 9, "is moved." should read --is moved,--

Claim 10, Column 14, Line 37, "is moved." should read --is moved,--

Signed and Sealed this

Thirteenth Day of July, 2010

David J. Kappos
*Director of the United States Patent and Trademark Office*